United States Patent
Jahn et al.

[11] Patent Number: 5,846,733
[45] Date of Patent: Dec. 8, 1998

[54] STRUCTURAL PHOSPHOPROTEIN (PP150) OF HUMAN CYTOMEGALOVIRUS, AND THE PREPARATION AND USE THEREOF

[75] Inventors: Gerhard Jahn, Neunkirchen; Birgit-Christine Scholl, Uttenreuth; Michael Bröker, Marburg; Michael Mach, Erlangen; Bernhard Fleckenstein, Schlaifhausen; Bernd Traupe, Hausen, all of Germany

[73] Assignee: Behring Diagnositcs GmbH, Marburg, Germany

[21] Appl. No.: 430,274

[22] Filed: Apr. 28, 1995

Related U.S. Application Data

[63] Continuation of Ser. No. 95,344, Jul. 23, 1993, abandoned, which is a continuation of Ser. No. 726,164, Jul. 2, 1991, abandoned, which is a continuation of Ser. No. 471,072, Jan. 29, 1990, abandoned, which is a continuation of Ser. No. 60,159, Jun. 10, 1987, abandoned.

[30] Foreign Application Priority Data

Jun. 12, 1986 [DE] Germany ............... 36 19 718.1

[51] Int. Cl.⁶ ............... C12N 15/38; G01N 33/53
[52] U.S. Cl. ............... 435/7.1; 435/7.92; 435/69.3; 530/350; 530/352; 530/324
[58] Field of Search ............... 435/69.1, 69.3, 435/69.7, 252.3, 240.2, 7.1, 7.92; 530/324, 350, 252

[56] References Cited

U.S. PATENT DOCUMENTS

| | | | |
|---|---|---|---|
| 4,554,159 | 11/1985 | Roizman et al. | 424/89 |
| 4,689,225 | 8/1987 | Pereira | 424/89 |
| 4,716,104 | 12/1987 | Harris et al. | 435/5 |
| 4,743,562 | 5/1988 | Rasmussen et al. | 424/89 |
| 4,762,780 | 8/1988 | Spector et al. | 435/172.1 |
| 4,769,331 | 9/1988 | Roizman et al. | 435/172.1 |
| 4,808,518 | 2/1989 | Dorsett et al. | 435/259 |

OTHER PUBLICATIONS

Landini et al., Microbiol. Immunol., vol. 30(7) pp. 683–695 (1986).
Chem Abs. vol. 101, 1984, 312 S.
Chem. Abs. vol. 101, 1984, 205 291 W.
Chem. Abs. vol. 103, 1985, 207739.
Chem. Abs. vol. 106, 1987, 16996 t.
Chem. Abs. vol. 108, 1988, 217994 k, Beach et al.
Chem. Abs. vol. 107, 19874, 37701 h, Jahn et al.
Chem. Abs. vol. 107, 1987, 110137 k, Jahn et al.
Gibson Virology, vol. 128, pp. 391–406, 1983.
Cremer et al. J. Clin. Microbiol. vol. 21, pp 517–521 (1985).
W. Gibson, Virol. 128:391–406 (1983).
R.A. Young and R.W. Davis, Proc. Natl. Acad. Sci. USA 80:1194–1198 (1983).
B. Fleckenstein et al., Gene 18:39–46 (1982).
Lardini et al, Microbiol. Zummonol. vol. 30 (7), pp. 683–695 ('86).
Chem. Abs. vol. 101, 1984, 312 s.
Chem. Abs. vol. 103, 1988, 207739 p.
Chem. Abs. vol. 106, 1989, 169906t.
Chem. Abs. vol. 108, 1988, 217994k, Bead et al.
Chem. Abs. vol. 107, 1987, 37701h, Sah. et al.
Chem Abs. vol. 107, 1987, 110139k, John et al.

(List continued on next page.)

Primary Examiner—Keith C. Furman
Attorney, Agent, or Firm—Finnegan, Henderson, Farabow, Garrett & Dunner, L.L.P.

[57] ABSTRACT

The phosphorylated structural protein of molecular weight about 150 kd (pp 150) of human cytomegalovirus (HCMV) is highly immunogenic and is reliably recognised by human antisera. This protein can, after assignment and sequencing of the gene, be prepared, in whole or in immunogenic sections, by gene manipulation. Proteins of this type are suitable as reagents, for example in an ELISA, and as constituents of vaccines.

8 Claims, 2 Drawing Sheets

```
Eco RI
GAATTCGATA CGGACGTGCG CCACGATGCC GAGATCGTGG AACGCGCGCT  50
CGTAAGCGCG GTCATTCTGG CCAAGATGTC GGTGCGCGAG ACGCTGGTCA  100
CAGCCATCGG CCAGACGGAA CCCATCGCCT TTGTGCACCT CAAGGATACG  150
GAGGTGCAGC GCATTGAAGA AAACCTGGAG GGTGTGCGCC GTAACATGTT  200
CTGCGTGAAA CCGCTCGACC TTAACCTGGA CCGGCACGCC AACACGGCGC  250
TGGTCAACGC CGTCAACAAG CTCGTGTACA CGGGCCGTCT CATCATGAAC  300
GTGCGCAGGT CTTGGGAGGA GCTCGAGCGC AAATGTCTGG CGCGCATTCA  350
GGAGCGCTGC AAGCTGCTGG TCAAGGAGCT GCGCATGTGC CTTTCCTTTG  400
ATTCCAACTA CTGTCGCAAT ATCCTCAAGC ACGCCGTGGA AAACGGCGAC  450
TCGGCCGACA CGCTGTTGGA GCTGCTCATC GAGGACTTTG ATATCTACGT  500
GGACAGCTTC CCACAGTCGG CGCACACGTT TTTGGCCGCG CGCTCGCCGT  550
CGTTGGAGTT TGACGATGAC GCCAATCTCC TCTCGCTCGG CGGCGGTTCG  600
GCCTTCTCGT CGGTACCCAA GAAACATGTC CCCACGCAGC CGCTGGACGG  650
CTGGAGCTGG ATCGCCAGTC CCTGGAAGGG ACACAAACCG TTCCGCTTCG  700
AGGCCCATGG TTCTCTGGCA CCGGCCGCCG AAGCCCACGC TGCCCGTTCG  750
GCGGCCGTCG GCTATTACGA CGAAGAGGAA AAGCGTCGCG AGCGGCAGAA  800
ACGGGTGGAC GACGAGGTGG TGCAGCGTGA GAAACAGCAG CTGAAGGCTT  850
GGGAGGAGAG GCAGCAGAAC CTGCAGCAAC GTCAGCAGCA ACCACCGCCC  900
CCGGCACGTA AACCGAGCGC CTCCCGGAGG CTCTTTGGCT CCAGTGCCGA  950
TGAGCACCAC GACGATGATG ATGACGAGAA AAACATCTTT ACGCCCATCA  1000
```

OTHER PUBLICATIONS

Gibson, *Virology* 128 ('83) pp. 391–406.
Cremer et al *J. Clin. Microb.* 21:517–521 '85.
Chemical Abstracts, vol. 108, 1988, 217994k, Bach et al.
Chem. Abs., vol. 107, 1987, 37701h, Jahn et al.
Chem. Abs., vol. 107, 1987, 110137k, Jahn et al.
Gibson, Virology 128, (1983), 391–406, Protein Counterparts of human and Simian Cytomegalovirus.
Landini et al, Microbiol. Immunol. vol. 30(7), pp. 683–695 (1986).

FIG. 1-1

```
Eco RI
GAATTCGATA CGGACGTGCG CCACGATGCC GAGATCGTGG AACGCGCGCT  50

CGTAAGCGCG GTCATTCTGG CCAAGATGTC GGTGCGCGAG ACGCTGGTCA 100

CAGCCATCGG CCAGACGGAA CCCATCGCCT TGTGCACCT CAAGGATACG 150

GAGGTGCAGC GCATTGAAGA AAACCTGGAG GGTGTGCGCC GTAACATGTT 200

CTGCGTGAAA CCGCTCGACC TTAACCTGGA CCGGCACGCC AACACGGCGC 250

TGGTCAACGC CGTCAACAAG CTCGTGTACA CGGGCCGTCT CATCATGAAC 300

GTGCGCAGGT CTTGGGAGGA GCTGGAGCGC AAATGTCTGG CGCGCATTCA 350

GGAGCGCTGC AAGCTGCTGG TCAAGGAGCT GCGCATGTGC CTTTCCTTTG 400

ATTCCAACTA CTGTCGCAAT ATCCTCAAGC ACGCCGTGGA AAACGGCGAC 450

TCGGCCGACA CGCTGTTGGA GCTGCTCATC GAGGACTTTG ATATCTACGT 500

GGACAGCTTC CCACAGTCGG CGCACACGTT TTTGGGCGCG CGCTCGCCGT 550

CGTTGGAGTT TGACGATGAC GCCAATCTCC TCTCGCTCGG CGGCGGTTCG 600

GCCTTCTCGT CGGTACCCAA GAAACATGTC CCCACGCAGC CGCTGGACGG 650

CTGGAGCTGG ATCGCCAGTC CCTGGAAGGG ACACAAACCG TTCCGCTTCG 700

AGGCCCATGG TTCTCTGGCA CCGGCCGCCG AAGCCCACGC TGCCCGTTCG 750

GCGGCCGTCG GCTATTACGA CGAAGAGGAA AAGCGTCGCG AGCGGCAGAA 800

ACGGGTGGAC GACGAGGTGG TGCAGCGTGA GAAACAGCAG CTGAAGGCTT 850

GGGAGGAGAG GCAGCAGAAC CTGCAGCAAC GTCAGCAGCA ACCACCGCCC 900

CCGGCACGTA AACCGAGCGC CTCCCGGAGG CTCTTTGGCT CCAGTGCCGA 950

TGAGGACGAC GACGATGATG ATGACGAGAA AAACATCTTT ACGCCCATCA 1000
```

FIG. 1-2

```
AGAAACCGGG AACTAGCGGC AAGGGCGCCG CTAGTGGTGG CGGTGTTTCC 1050

AGCATTTTCA GCGGCCTGTT ATCCTCGGGC AGTCAGAAAC CGACCAGCGG 1100

TCCCTTGAAC ATCCCGCAAC AACAACAGCG TCACGCGGCT TTCAGTCTCG 1150

TCTCCCCGCA GGTGACCAAG GCCAGCCCGG GAAGGGTCCG TCGGGACAGC 1200

GCGTGGGACG TGAGGCCGCT CACGGAGACC AGAGGGGATC TTTTCTCGGG 1250
                                              XhoII
CGACGAGGAT TCCGACAGCT CGGATGGCTA TCCCCCCAAC CGTCAAGATC 1300

CGCGTTTCAC CGACACGCTG GTGGACATCA CGGATACCGA GACGAGCGCC 1350

AAACCGCCCG TCACCACCGC GTACAAGTTC GAGCAACCGA CGTTGACGTT 1400

CGGCGCCGGA GTTAACGTTC CTGCTGGCGC CGGCGCTGCC ATCCTCACGC 1450

CGACGCCTGT CAATCCTTCC ACGGCCCCCG CTCCGGCCCC GACACCTACC 1500

TTCGCGGGTA CCCAAACCCC GGTCAACGGT AACTCGCCCT GGGCTCCGAC 1550

GGCGCCGTTG CCCGGGGATA TGAACCCCGC CAACTGGCCG CGCGAACGCG 1600

CGTGGGCCCT CAAGAATCCT CACCTGGCTT ACAATCCCTT CAGGATGCCT 1650

ACGACTTCCA CGGCTTCTCA AAACACCGTG TCCACCACCC CTCGGAGGCC 1700

GTCGACTCCA CGCGCCGCGG TGACACAAAC AGCGTCTCGG GACGCCGCTG 1750
                                         PstI
ATGAGGTTTG GGCTTTAAGG GACCAAACTG CAG                 1783
``` ic acid (IPTG). This resulted in formation of a fusion protein which
STRUCTURAL PHOSPHOPROTEIN (PP150) OF HUMAN CYTOMEGALOVIRUS, AND THE PREPARATION AND USE THEREOF This application is a continuation of application Ser. No. 08/095,344, now abandoned, filed Jul. 23, 1993; which is a continuation of application Ser. No. 07/726,164, now abandoned, filed Jul. 2, 1991, which is a continuation of application Ser. No. 07/471,072, now abandoned, filed Jan. 29, 1990, which is a continuation of application Ser. No. 07/060,159, now abandoned, filed Jun. 10, 1987.

BACKGROUND

A phosphorylated structural protein of about 150 kd (pp 150) is a constituent of purified virion particles. According to W. Gibson, Virology 128 (1983) 391–406, it is a constituent of the matrix. It is suitable as a diagnostic aid because of its strongly immunogenic properties.

The invention relates to pp 150 and immunogenic parts of this protein, to their preparation by gene manipulation and their use as an immunological reagent, for example in an ELISA. Preferred embodiments of the invention in their various aspects are explained in detail hereinafter and defined in the patent claims.

DESCRIPTION

It has been found that it is possible with a monospecific rabbit antiserum against pp 150 to identify the desired clones from a HCMV cDNA gene bank. For this purpose, a sample of the entire viral protein was subjected to preparative SDS polyacrylamide gel electrophoresis, and the individual protein bands were visualized using the dye-stuff $^R$Coomassie (ICI) brilliant blue. The protein with the molecular weight of 150 kd was cut out, extracted and used for immunizing rabbits. The antiserum which was obtained reacted with the 150 kd protein in a Western blot test. This serum was used to screen the cDNA gene bank.

To set up the gene bank, human preputial fibroblast cells were infected with HCMV, strain Ad 169, and, 96 to 120 hours after the infection, the poly(A)$^+$ RNA was isolated and converted into dsDNA and the latter was, without size fractionation, inserted into the commercially available phage expression vector λgt11. For this purpose, the vector was cleaved with EcoRI and treated with alkaline phosphatase (from calf intestine) to suppress intramolecular religation. By attachment of EcoRI linkers, the cDNA was inserted between the phage arms and packaged in vitro. In this way, from 100 ng of ds-cDNA was obtained a gene bank which contained about 5×10$^5$ independent recombinants and 18% wild type phages.

The gene bank was screened by the method of R. A. Young and R. W. Davis, Proc. Natl. Acad. Sci. USA 80 (1983) 1194–1198, but with the modification that horseradish peroxidase was coupled to protein A, and 4-chloro-1naphthol was used as detection system, employing the monospecific rabbit antibodies described above. In this "immunoscreening", the colonies present on nitro-cellulose filters are carefully lysed, incubated with the monospecific rabbit antibodies described above and, after removal of unbound reactants, positive plaques are detected using the modified detection system mentioned.

8 positive signals were obtained from 150,000 plaques examined. One clone with an insertion of about 300 bases was selected for further characterization; it was called BB 8.

The E. coli strain Y 1089 was infected with the recombinant phage, and the synthesis of the β-galactosidase protein was induced by addition of iso-propylthiogalactoside (IPTG). This resulted in formation of a fusion protein which is distinctly larger than galactosidase (118 kd). It is found neither in uninfected cells nor in infected but non-induced cells. Both human HCMV-positive sera and the rabbit anti-pp 150 serum reacted only with this protein in BB 8-infected, induced cells, but they did not recognize proteins either in uninfected or in non-induced infected cells. Thus, it is evident that the recombinant clone BB 8 synthesizes a fusion protein with a HCMV protein fraction.

The fusion protein from BB 8 was used to immunize a rabbit, and the antiserum was used to carry out Western Blot analyses with HCMV proteins. Only the pp 150 reacted.

The cDNA insertion of 300 bp was now used to locate the gene for pp 150 in the virus genome: for this purpose, the cDNA insertion of 300 bp was hybridized with 8 cosmid clones which encompass the entire genome of HCMV (B. Fleckenstein et al., Gene 18 (1982) 39–46). The cosmids pCM 1015 and pCM 1017, which contain the HindIII J, N and Y fragments with overlaps, hybridized with the cDNA. More detailed Southern blot analysis of this region localized the HCMV DNA fragment on a 1.5 kb EcoRI-PstI fragment which is located in the EcoRI Y fragment, specifically adjacent to the C fragment.

The cDNA of clone BB 8 was sequenced (Sanger's method). The DNA sequence is underlined in Table I (annex). It was possible, by comparison with the viral DNA sequence in this genomic region, to assign unambiguously to a long open reading frame which extends from nucleotide 524 to 3668 (Table I). Northern blot analyses with "late" RNA and $^{32}$P-labelled DNA of the clone BB 8 (recloned in M13) produced an abundant transcript of 6.2 kb.

Northern blot analyses with variously cloned viral DNA fragments from the HindIII J and N fragment produced various size classes of "late" RNA. The strongest signal was produced by a RNA in the 6.2 kb size class. Of all the structural proteins investigated, pp 150 was most reliably recognized by human HCMV-positive sera in Western blot analyses. In these there were reactions both with IgM-positive and with IgG-positive sera from a very wide variety of patients, for example children with congenital infections, AIDS patients as well as symptomatic and asymptomatic people.

Since it would be possible only with great technical elaboration to isolate pp 150 in the amounts necessary for diagnostic aids, the manner of preparation by gene manipulation according to the invention is especially advantageous. It has emerged that antigenic activity is shown not only by products expressed by eukaryotic cells but also by bacterial expression products. Since bacteria do not produce phosphoproteins, it could not have been expected that HCMV pp 150, or parts thereof, produced by bacteria also has strong immunogenic activity. However, it emerged that such proteins are also just as unambiguously recognized by appropriate sera as is authentic pp 150.

Thus, it is possible according to the invention to use pp 150, or immunogenic parts thereof, which has been prepared in prokaryotic or eukaryotic cells, for example yeast cells, human or animal cells, as a reagent for detecting HCMV antibodies, for example in an ELISA.

BRIEF DESCRIPTION OF THE DRAWING

FIG. 1 shows the cDNA sequence of the EcoRI Y fragment of HCMV.

PREFERRED EMBODIMENTS

EXAMPLE

The XhoII-PstI fragment which is located inside the HCMV EcoRI Y fragment and thus codes for parts of pp 150 was ligated in the expression vector pBD 2 (M. Bröker, Gene Anal. Techn. 3 (1986) 53–57) after the vector had been cleaved with BamHI and PstI.

Transformation of the resulting hybrid plasmid into *E. coli* BMH 71-18 was followed by isolation of clones whose plasmid DNA had the expected restriction pattern. After induction of the lac promoter with isopropyl-β-D-thiogalactopyranoside (IPTG) the clones expressed large amounts of a fusion protein having a pp 150 fraction.

The new plasmid which codes for this β-galactosidase-pp 150 fusion protein is called pXP1 hereinafter. The fusion protein coded for by pXP1 was isolated from *E. coli* cells which contain the vector pXP1 after induction with IPTG, and was used for immunizing rabbits. Serum obtained after three immunizations reacted in Western blot analyses with protein bands of about 150,000 d from HCMV-infected cell extracts but not with control extracts. Thus, antibodies raised against the pp 150 synthesized by bacteria are able to recognize authentic pp 150. In addition, it was possible to use the anti-pXP1 serum to detect HCMV by immunofluorescence only two or three days after infection of cell cultures, whereas the cytopathic effect is not detectable until ten to fourteen days have elapsed. Thus, a serum obtained using pp 150 prepared by recombination can be used as a diagnostic agent.

We claim:

1. A recombinant polypeptide, obtained by expression of a DNA molecule encoding the HCMV structural phosphoprotein with a molecular weight of 150 kd (pp 150), which is located in the region of the fragments HindIII J/N of the genome of HCMV, strain Ad 169, in a nonhuman cell, wherein the polypeptide will bind to an antibody directed against HCMV.

2. A recombinant polypeptide, obtained by expression of a DNA molecule encoding the HCMV structural phosphoprotein with a molecular weight of 150 kd (pp 150), which is located on a 1.5 kb EcoRI-PstI fragment inside the EcoRI Y fragment from the genome of HCMV, strain Ad 169, in a nonhuman cell, wherein the polypeptide will bind to an antibody directed against HCMV.

3. A recombinant structural polypeptide as in claim 1, wherein said polypeptide is obtained by expression of the gene in a prokaryotic cell.

4. A recombinant structural polypeptide as in claim 2, wherein said polypeptide is obtained by expression of the gene in a prokaryotic cell.

5. A recombinant polypeptide as claimed in claim 2, wherein said polypeptide has an amino acid sequence encoded by the DNA sequence shown in FIG. 1.

6. A recombinant polypeptide fragment of the polypeptide claimed in claim 2, wherein said polypeptide fragment has an amino acid sequence encoded by the XhoII-PstI fragment shown in FIG. 1.

7. A method for detecting the presence or absence of antibodies that bind to the pp 150 antigen of human cytomegalovirus comprising:

(a) contacting the isolated recombinant polypeptide as claimed in claims 1, 2, 3, 4, 5 or 6 with a biological sample for a time and under conditions sufficient for the polypeptide and antibodies in the biological sample form a complex; and (b) detecting the complex formed.

8. The method of claim 7 wherein the method is an ELISA.

* * * * *